United States Patent
Kobayashi et al.

(10) Patent No.: US 8,333,189 B2
(45) Date of Patent: Dec. 18, 2012

(54) LIQUID MEDICINE RESERVOIR AND DISCHARGING DEVICE FOR LIQUID MEDICINE TO BE INHALED

(75) Inventors: Masaya Kobayashi, Yokohama (JP); Nobuo Oshimoto, Kawasaki (JP); Masahiro Takei, Kawasaki (JP); Masaru Sugita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 575 days.

(21) Appl. No.: 12/565,055

(22) Filed: Sep. 23, 2009

(65) Prior Publication Data

US 2010/0071691 A1    Mar. 25, 2010

(30) Foreign Application Priority Data

Sep. 24, 2008  (JP) ................. 2008-244193

(51) Int. Cl.
*A61M 11/00* (2006.01)
*A61M 16/00* (2006.01)

(52) U.S. Cl. ......... 128/200.22; 128/200.14; 128/200.24; 128/203.12; 128/203.15

(58) Field of Classification Search .......... 128/200.11–200.22, 200.24, 203.12, 128/203.15, 203.21; 604/110, 195; 215/14–30, 215/901; 206/363–370
See application file for complete search history.

(56) References Cited

U.S. PATENT DOCUMENTS

| | | | |
|---|---|---|---|
| 4,728,321 A | 3/1988 | Chen | |
| 4,781,683 A | 11/1988 | Wozniak | |
| 5,312,348 A | 5/1994 | Sans | |
| 5,403,289 A * | 4/1995 | Berrebi et al. | 604/232 |
| 5,413,564 A * | 5/1995 | Silver et al. | 604/232 |
| 5,474,885 A * | 12/1995 | Michiels et al. | 430/539 |
| 5,515,842 A * | 5/1996 | Ramseyer et al. | 128/200.18 |
| 8,080,098 B2 * | 12/2011 | Kurihara et al. | 106/31.25 |

FOREIGN PATENT DOCUMENTS

| | | |
|---|---|---|
| GB | 2284554 | 6/1995 |
| JP | 2004-283245 A | 10/2004 |
| JP | 2004-290593 A | 10/2004 |
| JP | 2005-27884 A | 2/2005 |
| JP | 2005-512639 T | 5/2005 |
| JP | 2006-102970 A | 4/2006 |
| JP | 2007-520297 T | 7/2007 |
| WO | WO91/00749 | 1/1991 |
| WO | WO03051440 | 6/2003 |
| WO | WO2005075103 | 8/2005 |
| WO | WO2008/016156 | 2/2008 |
| WO | WO2009/014153 | 1/2009 |

* cited by examiner

*Primary Examiner* — Annette Dixon
(74) *Attorney, Agent, or Firm* — Canon U.S.A., Inc., IP Division

(57) ABSTRACT

A liquid medicine reservoir that supplies liquid medicine to a liquid-medicine discharging portion via a communicating portion includes a cylindrical body configured to hold the liquid medicine therein, a first sealing portion to which the communicating portion is connected, the first sealing portion sealing the cylindrical body, and a second sealing portion configured to seal an end of the cylindrical body opposite the first sealing portion. At least one of the first sealing portion and the second sealing portion move relative to each other in accordance with the amount of liquid medicine. A substance configured to inhibit discharging of the liquid medicine is stored in a space in the cylindrical body that is on an inner side of the second sealing portion and that is separate from the liquid medicine.

8 Claims, 11 Drawing Sheets

MOVING DIRECTION OF MOVABLE GASKET 4

FIG. 3A
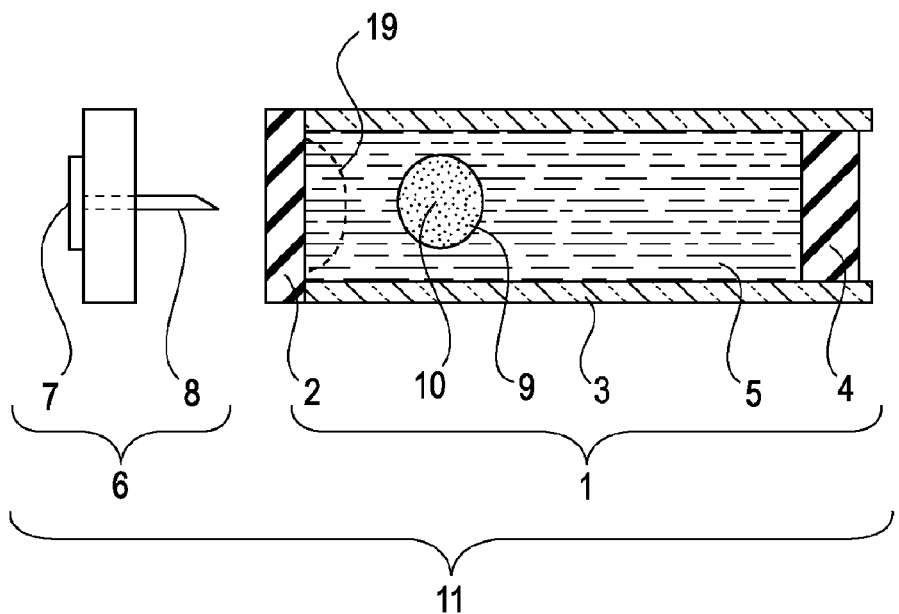
FIG. 3B
MOVING DIRECTION OF MOVABLE GASKET 4
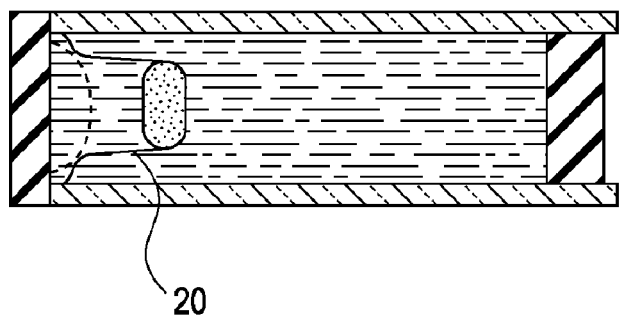
FIG. 3C
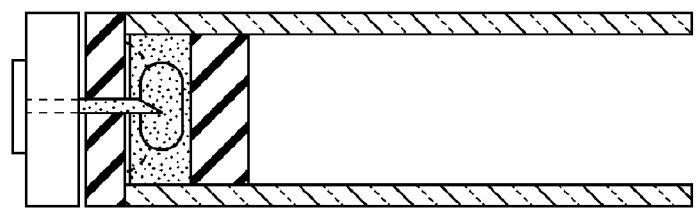

FIG. 5A
FIG. 5B
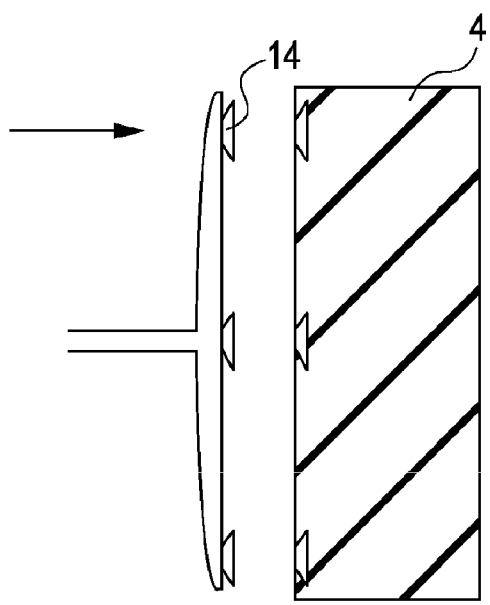
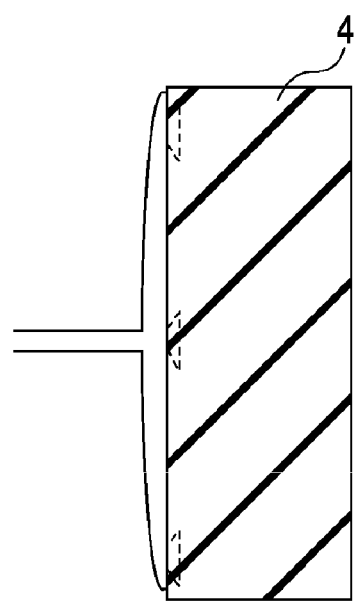

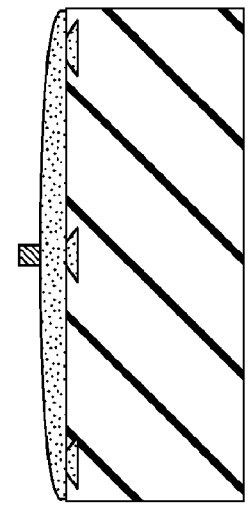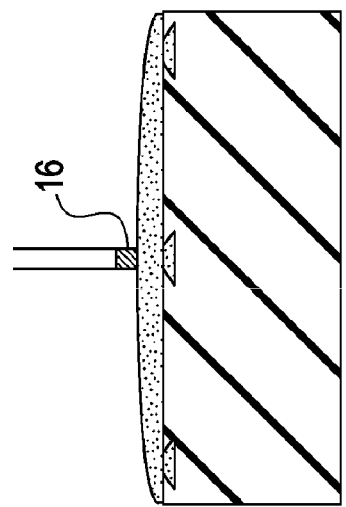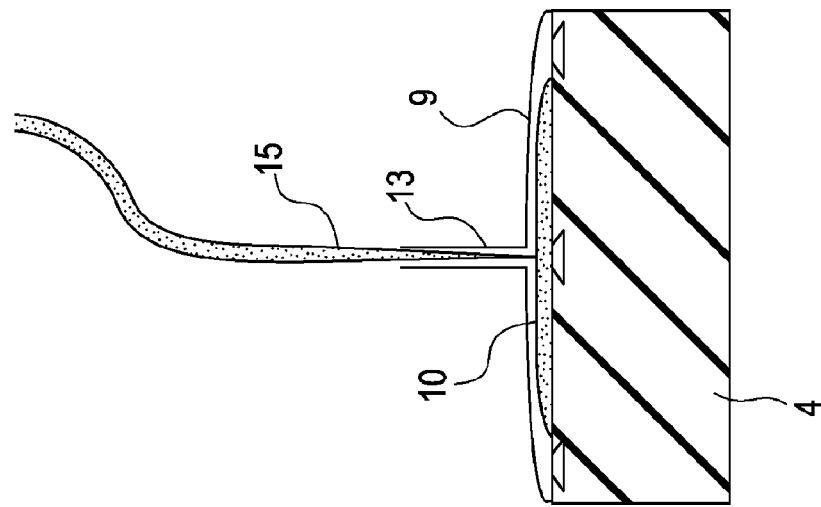

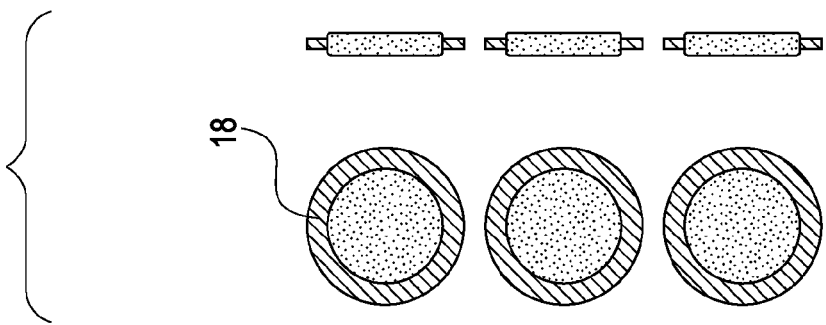
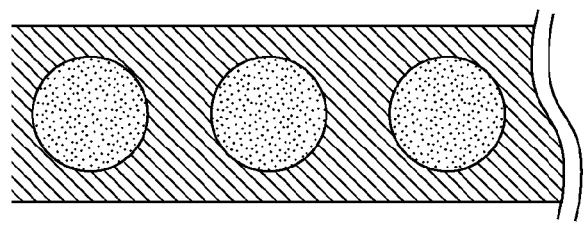
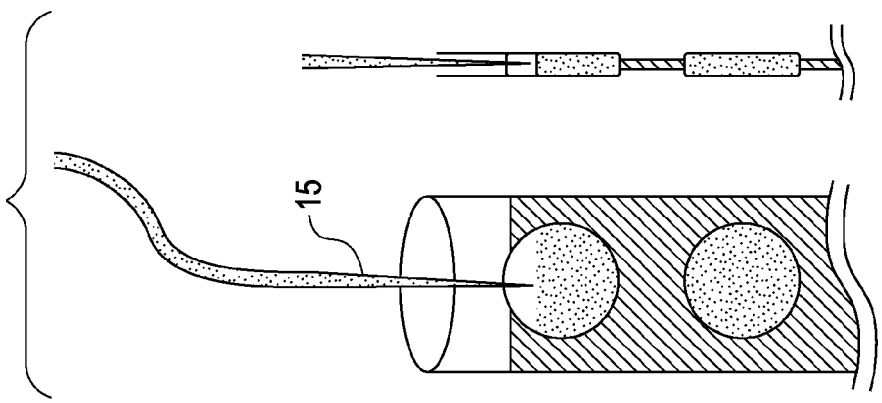
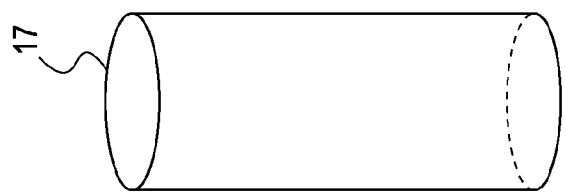

LIQUID MEDICINE RESERVOIR AND DISCHARGING DEVICE FOR LIQUID MEDICINE TO BE INHALED

BACKGROUND OF THE INVENTION

1. Field of the Invention

The present invention relates to a liquid medicine reservoir containing liquid medicine, and to a discharging device for liquid medicine to be inhaled.

2. Description of the Related Art

Liquid-medicine discharging devices that help the user to inhale liquid medicine have been developed. The liquid-medicine discharging devices discharge the liquid medicine in the form of minute droplets into an air passage, through which air sucked via a mouthpiece flows, by utilizing the discharging principle of an inkjet method. These discharging devices for liquid medicine to be inhaled can accurately discharge a predetermined amount of liquid medicine in the form of droplets of a uniform diameter.

As a specific example of a discharging device for liquid medicine to be inhaled, Japanese Patent Laid-Open Nos. 2004-290593 and 2004-283245 disclose liquid medicine cartridges including a discharging head (liquid-medicine discharging unit) in which a discharging-energy generating element, such as a heat generating element, is provided, and a liquid medicine reservoir that contains liquid medicine to be supplied to the discharging head.

In the liquid medicine cartridges of the related art, however, the liquid medicine reservoir can be refilled with the same liquid medicine or another liquid medicine after use, and can be reused along with the discharging head. For this reason, the liquid medicine reservoir and the discharging head may be used more than a specified number of times.

SUMMARY OF THE INVENTION

According to one aspect of the invention, a liquid medicine reservoir that supplies liquid medicine to a liquid-medicine discharging portion via a communicating portion is provided. The liquid medicine reservoir includes a cylindrical body configured to hold the liquid medicine therein, a first sealing portion to which the communicating portion is connected, the first sealing portion sealing the cylindrical body, and a second sealing portion configured to seal an end of the cylindrical body opposite the first sealing portion. At least one of the first sealing portion and the second sealing portion move relative to each other in accordance with an amount of the liquid medicine. A substance configured to inhibit discharging of the liquid medicine is stored in a space in the cylindrical body that is on an inner side of the second sealing portion and that is separate from the liquid medicine.

Further features of the present invention will become apparent from the following description of exemplary embodiments with reference to the attached drawings.

BRIEF DESCRIPTION OF THE DRAWINGS

FIG. 1A is a conceptual view of the liquid medicine reservoir before a discharging head is connected thereto, FIG. 1B is a conceptual view of the liquid medicine reservoir after the discharging head is connected thereto, and FIG. 1C is a conceptual view showing a state of the liquid medicine reservoir into which a sharp needle member is stuck from a side of the liquid medicine reservoir opposite a side toward which a movable gasket moves.

FIGS. 3A, 3B, and 3C conceptually show configurations of a liquid medicine reservoir according to another embodiment of the present invention, FIG. 3A shows an embodiment in which a bag containing a discharging inhibitor is floating in liquid medicine, FIG. 3B shows a modification of the embodiment in which a floating area of the bag is limited, and FIG. 3C is a cross-sectional view showing a state in which the bag is broken by a communication needle by moving a movable gasket forward.

FIGS. 4A to 4C show a bag produced by blow molding.

FIGS. 5A and 5B show a method for fixing the produced bag to a movable gasket, FIG. 5A shows a fixing method using press fitting, and FIG. 5B shows formation of the movable gasket on the bag.

FIGS. 6A to 6C are conceptual views illustrating a method for filling a movable gasket, to which a bag is fixed, with a discharging inhibitor and a sealing method.

FIGS. 7A to 7D are conceptual views showing a method for producing a bag by pillow packaging.

FIGS. 8A to 8C are conceptual views showing a state in which a bag produced by pillow packaging is fixed to a movable gasket, FIG. 8A is a front view of the bag, FIG. 8B is a side view of the bag fixed to the movable gasket, and FIG. 8C is a conceptual view showing a state of a periphery sealing portion folded inward when set in a barrel.

FIGS. 9A to 9E are conceptual views showing the configuration and operation of a liquid medicine cartridge including a liquid medicine reservoir having the configuration shown in FIG. 3B.

FIG. 10 is a perspective view showing the outer appearance of an inhaler serving as an example of a liquid-medicine discharging device to which the liquid medicine reservoir of the present invention is applied, which inhaler helps the user to inhale liquid medicine.

FIG. 11 is a perspective view showing a state in which an access cover is open in the liquid-medicine discharging device shown in FIG. 10.

DESCRIPTION OF THE EMBODIMENTS

Aspects of the present invention will be described in more detail below with reference to the drawings. In principle, like components are denoted by like reference numerals, and descriptions thereof are omitted.

FIGS. 1A, 1B, and 1C are schematic cross-sectional views conceptually showing the configuration of a liquid medicine reservoir 1 according to a first embodiment in accordance with aspects of the present invention. A main body of the liquid medicine reservoir 1 is formed by a rigid cylindrical body (barrel) 3 made of, for example, glass. According to aspects of the present invention, the cylindrical body is not limited to a cylindrical member, and may also be shaped like, for example, a prism, such as a triangular prism or a quadrangular prism. That is, the cylindrical body may have any shape as long as it is hollow. The barrel 3 is hermetically closed at one end by a fixed gasket (fixed sealing portion) 2 serving as a first sealing portion. A discharging head 6 can be connected to the fixed gasket 2 by a communication needle 8 serving as a communicating portion. FIGS. 1A and 1B are conceptual views showing, respectively, states before and after the discharging head 6 is connected. Connection allows liquid medicine 5 contained in the liquid medicine reservoir 1 to be supplied to the discharging head 6 via the communication needle 8 and to be discharged from a discharging port 7. The liquid medicine reservoir 1 and the discharging head 6 constitute a liquid medicine cartridge 11.

Figure 1A:
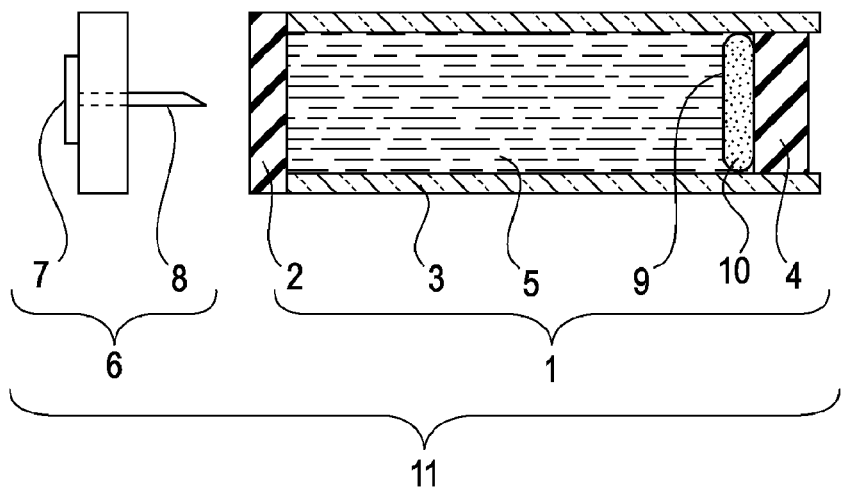
FIGS. 1A to 1C conceptually show a configuration of a liquid medicine reservoir according to an embodiment of the present invention.

A discharging-energy generating element that generates energy for discharging the liquid is provided near the discharging port 7 from which the liquid medicine 5 is discharged. The discharging-energy generating element applies a discharging energy to the liquid that has passed through the communication needle 8, whereby the liquid is discharged from the discharging port 7.

While an arbitrary element can be used as the discharging-energy generating element, an electrothermal transducer for applying heat energy to the liquid or an electromechanical transducer for applying mechanical energy to the liquid can be used, as an example. That is, discharging can be performed by a method (e.g., thermal jet method) for discharging the liquid by applying heat energy to the liquid with an electrothermal transducer, or by a method (e.g., piezo-jet method) for discharging the liquid by using vibratory pressure of an electromechanical transducer (e.g., a piezoelectric element) for applying mechanical energy to the liquid. The discharging method can be selected, for example, according to the kind of liquid.

The use of a thermal jet method makes it possible to increase the bore diameter of the discharging port, the quantity of heat pulse used for discharging, the size precision of the electrothermal transducer such as a micro heater, and reproducibility in each discharging head. Hence, a relatively narrow droplet diameter distribution can be achieved. Further, high applicability to small devices that require low head manufacturing cost and frequent head replacement may also be achieved. Accordingly, when the liquid medicine reservoir of the embodiment is applied to a liquid-medicine discharging device that requires high portability and convenience, it may be the case that thermal jet discharging is adopted.

A movable gasket (movable sealing portion) 4 serving as a second sealing portion is provided at an end of the barrel 3 opposite the fixed gasket 2. When the liquid medicine reservoir 1 is connected to the discharging head 6, the interior of the liquid medicine reservoir 1 is isolated from outside air except at the discharging port 7. Hence, when the liquid medicine 5 is discharged from the discharging port 7 and the amount of liquid medicine 5 remaining in the liquid medicine reservoir 1 decreases, a pressure difference is formed between the interior and exterior of the liquid medicine reservoir 1. When the pressure difference reaches a predetermined value, the movable gasket 4 can move into the liquid medicine reservoir 1 so as to reduce the pressure difference. When the movable gasket 4 moves, the capacity of the liquid medicine reservoir 1 decreases to maintain a constant pressure difference between the interior and exterior of the liquid medicine reservoir 1. The use of the movable gasket 4 eliminates the necessity for communication of the interior of the liquid medicine reservoir 1 with the air except at the discharging port 7, and this may prevent undesirable changes of the liquid medicine 5 due to reaction between the liquid medicine 5 and the air, and leakage of the liquid medicine 5.

The movable gasket 4 can have thickness and elasticity that allows the liquid medicine 5 to be sufficiently sealed in the liquid medicine reservoir 1. The movable gasket 4 may be formed for example by an elastic member, such as a rubber stopper.

Figure 1B:
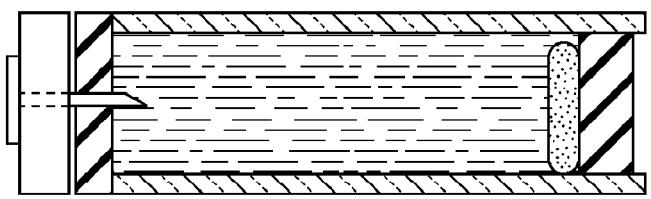

Aspects of the present invention may be characterized in that a discharging inhibitor 10 for inhibiting discharging of the liquid medicine is stored in a space provided in the barrel (cylindrical body) 3, on an inner side of the movable gasket 4, and separately from the liquid medicine. FIGS. 1 and 2 show an example in which the discharging inhibitor is stored in a bag 9 fixed to the movable gasket 4. However, the space containing the discharging inhibitor is not limited to the above-described bag. Alternatively, for example, a chamber for the discharging inhibitor that is divided from the space containing the liquid medicine by a film may be provided on the inner side of the movable gasket 4.

Here, the term "the inner side of the movable gasket 4" refers to an inner side of the liquid medicine reservoir located on the interior side of the movable gasket 4, that is, a side where the liquid medicine is stored. By being formed on the inner side of the movable gasket 4, the space containing the discharging inhibitor itself may not need to communicate with the air, and this can prevent deterioration of the discharging inhibitor.

Aspects of the present invention will be described in more detail below with reference to FIG. 2. When the movable gasket 4 further moves forward after the user takes (e.g., inhales) the liquid medicine 5 a specified number of times, as shown in FIG. 2, the communication needle 8 breaks the bag 9. Then, the discharging inhibitor 10 flows through the communication needle 8, and clogs the discharging port 7, whereby discharging becomes impossible. In other words, the term "discharging inhibitor" according to aspects of the present invention refers to a composition that cannot be discharged by the discharging-energy generating element provided in the discharging head 6, and that may be put into the discharging head 6 to inhibit the liquid medicine from being discharged from the discharging head 6. Examples of discharging inhibitors will be given below.

The present invention is not limited to the above-described manner in which the space (e.g., bag 9) containing the discharging inhibitor is broken by the communication needle 8. For example, it may be the case that it is only necessary that the movable gasket 4 moves toward the inner side of the reservoir, that the capacity of the reservoir decreases, and that the discharging inhibitor is finally supplied to the discharging head 6. For example, when the capacity of a reservoir that runs out of the liquid medicine 5 is smaller than that of the bag 9, the bag 9 may be broken by movement of the movable gasket 4, and this may allow the discharging inhibitor to be supplied to the discharging head 6.

Figure 1C:
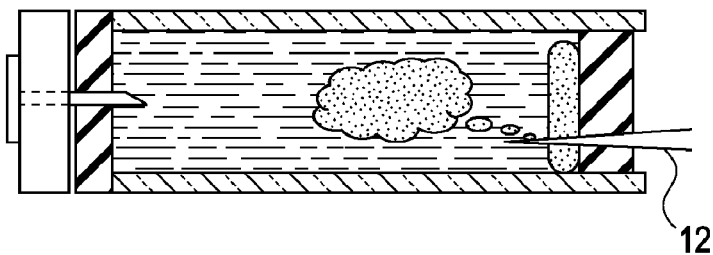
Figure 2:
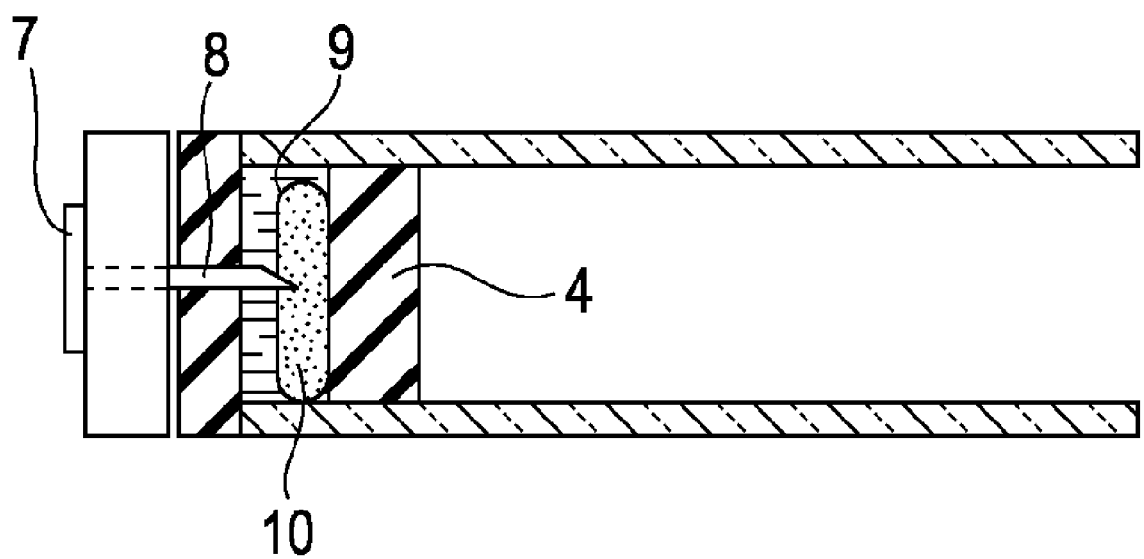
FIG. 2 is a cross-sectional view showing a state in which a bag is broken by a communication needle by further moving the movable gasket after liquid medicine is taken (inhaled) a specified number of times.

FIG. 1C shows a state in which a sharp needle member 12 is stuck into the liquid medicine reservoir from a side of the liquid medicine reservoir 1 opposite a side toward which the movable gasket 4 moves. When the sharp needle member 12 is stuck to add or remove the liquid medicine 5 into or from the liquid medicine reservoir 1, the discharging inhibitor in the bag 9 disperses into the barrel 3. In such a case in which the space containing the discharging inhibitor is provided between the space containing the liquid medicine and the movable gasket 4, the liquid medicine 5 can be prevented from being removed and replaced with another liquid medicine before inhalation. That is, it may be the case that the space containing the discharging inhibitor is in contact with the movable gasket without the liquid reservoir being disposed therebetween, for example, the bag 9 may be fixed to the movable gasket 4, as in aspects of the first embodiment. It may also be the case that the space containing the discharging inhibitor is fixed in a manner such as to cover the entire surface of the movable gasket 4. In this case, the needle member 12 hits the space containing the discharging inhibitor, regardless of the position on the movable gasket side where the needle member 12 is stuck.

According to aspects of the first embodiment, the first sealing portion for sealing the side of the cylindrical body (barrel 3) to which the communicating portion is connected is the fixed sealing portion fixed to the cylindrical body, and the second sealing portion for sealing the end opposite the first sealing portion is the movable sealing portion that is movable in accordance with the amount of liquid medicine. However, the present invention is not limited to this structure. That is, it may be the case that the first and second sealing portions are movable relative to each other in accordance with the amount of liquid medicine. The first sealing portion may be a movable sealing portion that is movable in accordance with the amount of liquid medicine, and the second sealing portion may be a fixed sealing portion fixed to the cylindrical body.

According to one aspect of the invention, as the space containing the discharging inhibitor, the bag 9 may be desirable because the bag 9 may be made thin enough to be broken relatively easily.

Accordingly, aspects of the present invention provide a liquid medicine reservoir that can prevent wrong reuse of a liquid medicine cartridge. Aspects of the present invention may also provide a liquid medicine reservoir where, after a specified correct use of the liquid medicine, the discharging head is clogged with a substance for preventing discharging of the liquid medicine. Thus, reuse of the liquid medicine cartridge can be prevented.

FIGS. 3A, 3B, and 3C conceptually show the configuration of a liquid medicine reservoir according to another embodiment of the present invention. FIGS. 3A and 3B are conceptual views showing states before a discharging head 6 is connected. FIG. 3A shows a second embodiment in which a bag 9 containing a discharging inhibitor is floating in liquid medicine 5. The bag 9 is protected by a mesh 19 from being accidentally broken by a communication needle 8 before the liquid medicine 5 is inhaled a specified number of times. The mesh 19 may be fixed to a fixed gasket 2 or an inner wall of a barrel 3.

FIG. 3B shows a modification of the second embodiment. In this modification, an area where the bag 9 containing the discharging inhibitor floats is limited. While a discharging device for liquid medicine to be inhaled functions without problems even when the bag 9 is not fixed, as shown in FIG. 3A, it may be that a user prefers that the bag 9 be present at a position which is out of sight of the user, so that the bag 9 does not attract the user's attention. For that purpose, according to one aspect, one end of a floating-area regulating member 20 is connected to the bag 9, and the other end is connected to the fixed gasket 2 or the inner portion of the barrel 3. The floating-area regulating member 20 can be formed of any material that has no influence on liquid medicine 5. For example, the floating-area regulating member 20 can be formed of resin, such as polyethylene, polypropylene, or nylon, or a metal coated with resin.

FIG. 3C is a cross-sectional view showing a state in which a movable gasket 4 further moves forward and a communication needle 8 breaks the bag 9 after the liquid medicine 5 is taken (e.g., inhaled) a specified number of times in the modification shown in FIG. 3B. In this case, the mesh 19 is pushed and deformed by the movable gasket 4. It may be the case that the openings of the mesh 19 are larger than the communication needle 8. While the mesh 19 can be formed of the same material as that of the above-described floating-area regulating member 20, it may also be the case that the mesh 19 is inflexible (i.e., maintains its shape without deforming under its own weight).

Material of Bag 9

Next, embodiments of the material of the bag 9 will be described. According to one aspect, the bag 9 may hold the liquid medicine 5 and the discharging inhibitor apart with one film disposed therebetween. Hence, it may be the case that it is necessary to select, as the material of the bag 9, a film that has high barrier performance for gas and vapor. According to one aspect, when the sharp needle 12 is stuck into the liquid medicine reservoir 1, the bag 9 should not be stretched and the discharging inhibitor should disperse into the liquid medicine 5. Therefore, it may be important that the film used for the bag 9 can be torn. Also, thickness reduction of the film may be more effective for sticking of the sharp needle 12. Examples of materials that satisfy these conditions of barrier performance and tearablility comprise one or more of a polypropylene film coated with polyvinylidene chloride, a three-layer laminate film of polyethylene terephthalate (PET), ethylene-vinyl alcohol (EVOH), and low-density polyethylene (LDPE), a three-layer laminate film of nylon (Ny), ethylene-vinyl alcohol (EVOH), and low-density polyethylene (LDPE), a three-layer laminate film of polypropylene (PP), ethylene-vinyl alcohol (EVHO), and low-density polyethylene (LDPE), an aluminum-evaporated PET film, a silica-evaporated PET film, and a silica-evaporated nylon film. For example, since a film evaporated with silica or alumina can be thinned to several tens of micrometers, it may be suitably used according to aspects of the present invention.

Production Method for Bag 9

Figure 8A:
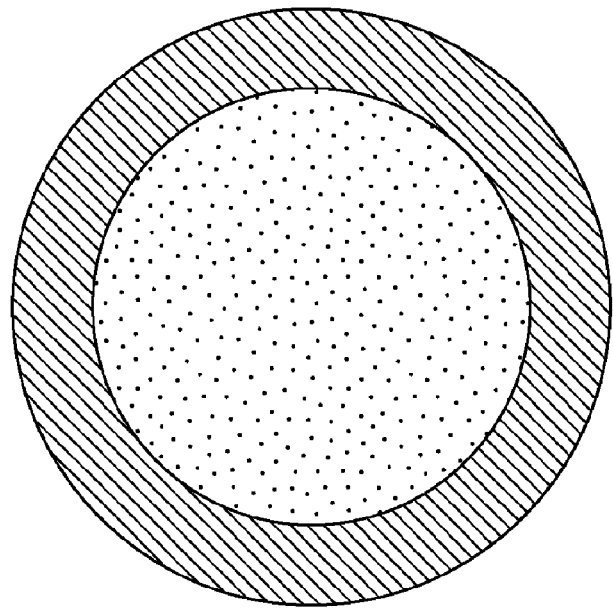

An embodiment of a production method for the bag 9 and a fixing method for fixing the bag 9 to the movable gasket 4, as shown in FIG. 1 will be described with reference to FIGS. 4 to 8. FIGS. 4 to 6 show an example of a method for producing the bag 9 by blow molding and a method for fixing the bag 9 to the movable gasket 4, and FIGS. 7 and 8 show an example of a method for producing the bag 9 by pillow packaging and a method for fixing the bag 9 to the movable gasket 4.

Figure 4C:
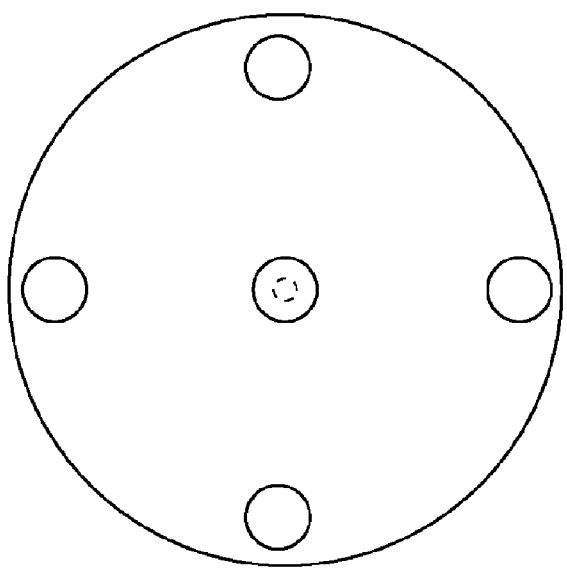
Figure 4B:
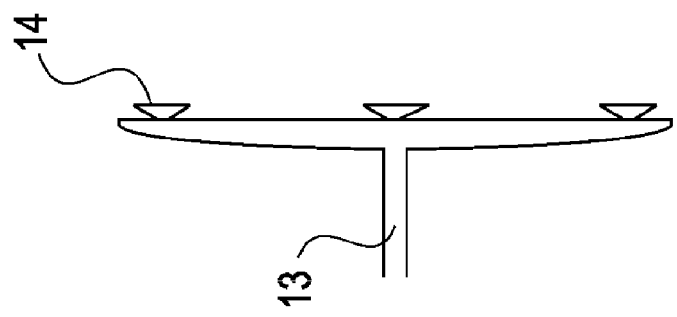
Figure 4A:
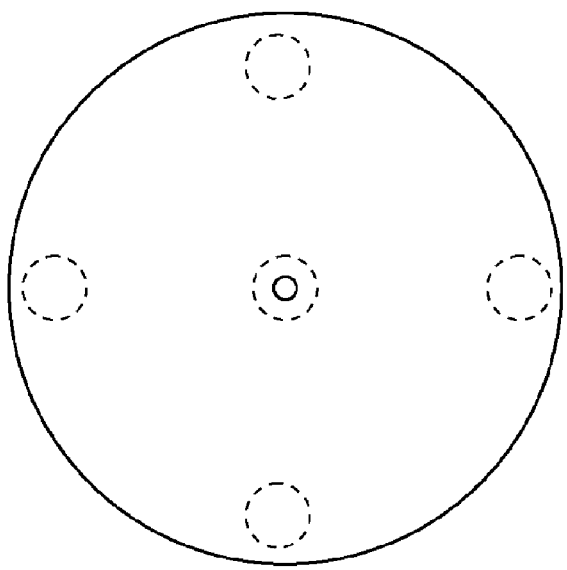

First, descriptions will be given of the method for producing the bag 9 by blow molding and the method for fixing the bag 9 to the movable gasket 4. FIGS. 4A to 4C show an example of a bag 9 produced by blow molding. FIGS. 5A and 5B show two methods for fixing the produced bag 9 to the movable gasket 4.

Blow molding is a molding method for thermoplastic resin, and is also called hollow molding. The material of a bag is melted into the shape of a pipe, is extruded into a molding die, and air is blown into the pipe to form a hollow structure. In this case, it may be that anchor projections 14 for fixing the bag to the movable gasket 14 are formed at at least five positions. The anchor projections 14 allow the bag 9 to be in as close contact with the movable gasket 4 as possible when fixed to the movable gasket 4, and may prevent the bag 9 from being raised when the sharp needle 12 is stuck into the liquid medicine reservoir 1. The anchor projections 14 may be tapered like a truncated cone, so as not be easily pulled off. An opening from which air is blown during molding is used as a sealing port 13 when the discharging inhibitor 10 is sealed in a later process. The bag 9 can be fixed to the movable gasket 4 by press-fitting the anchor projections 14 into corresponding engaging portions provided in the movable gasket 4, as shown in FIG. 5A. Alternatively, the movable gasket 4 can be combined with the bag 9 by pouring a rubber material over the anchor projections 14 of the bag 9, as shown in FIG. 5B.

FIGS. 6A to 6C show methods for filling and sealing the discharging inhibitor 10 in the bag 9 fixed to the movable gasket 4. The discharging inhibitor 10 may be filled in the form of liquid or powder from the sealing port 13 with a discharging-inhibitor filling member 15. After filling, the sealing port 13 is closed to form a sealing-port closing portion 16. Finally, an unnecessary portion of the sealing port 13 may be cut, so that the movable gasket 4 is provided with the bag 9 filled with the discharging inhibitor 10.

Figure 8B:
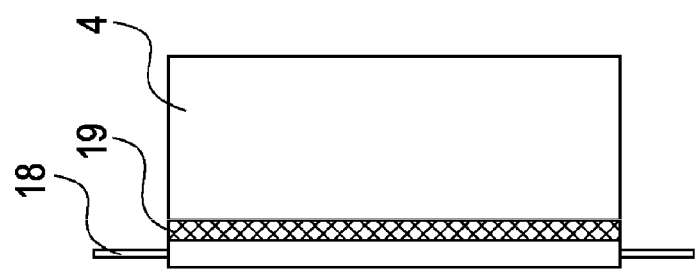
Figure 8C:
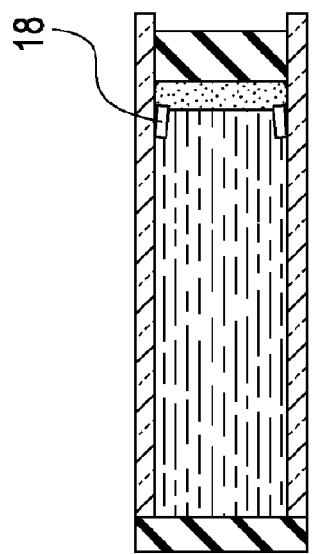

Next, descriptions will be given of a method for producing the bag 9 by pillow packaging and a method for fixing the bag 9 to the movable gasket 4. FIGS. 7A to 7D show a method for producing a bag 9 by pillow packaging. A cylindrical bag material 17 is prepared, and is set in a pillow packaging machine (not shown). In parallel with heat welding, a discharging inhibitor 10 is sequentially filled using a discharging-inhibitor filling member 15. After filling and sealing, unnecessary portions of a semifinished bag except peripheral sealing portions 18 may be cut, thus producing bags 9 by pillow packaging. Each produced bag 9 may be fixed to the movable gasket 4 with an adhesive 19, as shown in FIG. 8B. As shown in FIG. 8C, the peripheral sealing portion 18 is folded inward to hold the liquid medicine 5 with the movable gasket 4 so that the liquid medicine 5 will not leak when the movable gasket 4 is set in the barrel 3.

Discharging Inhibitor

An embodiment of the discharging inhibitor 10 stored in the bag 9 will now be described. The discharging inhibitor 10 may be in the form of liquid or powder.

A liquid serving as the discharging inhibitor may be, for example, an edible viscosity modifier. Since the viscosity of the liquid medicine contained in the liquid-medicine discharging device is typically about 1 mPa·s, the viscosity of the discharging inhibitor may be set at 3 mPa·s or more, such as 10 mPa·s or more, and even such as 30 mPa·s or more. A high-viscosity solution to which such liquid is added clogs the discharging port 7, and makes discharging impossible. An example of an edible viscosity modifier is xanthan gum. Since liquids like oil have a viscosity higher than that of the liquid medicine 5, they may clog the discharging port 7 having an opening of several micrometers, and make discharging impossible.

Examples substances suitable for the discharging inhibitor can include at least one of a water-absorbing polymer, a gelatinizer, and a thickening agent. For example, powders suitable as the discharging inhibitor may be polyvinyl alcohol and sodium polyacrylate serving as water-absorbing polymers. These materials cake by absorbing the liquid medicine 5, clog the nozzle, and can make discharging impossible. Gelatinizer containing starch, such as flour, dogtooth violet starch, corn starch, or potato starch, may also clog the nozzle in the form of powder. Also, when discharging is performed, the gelatinizer may become gelatinized by the heat energy conversion element to make discharging impossible. Thickening agents and gelling agents, such as for example gelatin or agar, may also provide the same advantages as those of the above-described starches.

Further, a powder of pigment or dye or a solution containing pigment or dye of, for example, red color, may be stored in the bag 9 so as to change the color of the liquid medicine 5 for visual recognition when the bag 9 is broken. By mixing in pigment or dye, a visual warning about failure in the liquid medicine reservoir can be given. For example, edible tar colors, namely, one or more of amaranth, tartrazine, fast green FCF, and brilliant blue FCF, can be used.

Although the kind of liquid medicine 5 is not limited, when the liquid medicine reservoir of the present invention is used for a liquid-medicine discharging device, a liquid medicine for treatment can be used. Here, the term "liquid medicine" conceptually includes not only medicinal compounds having pharmacological and physiological functions, but also flavoring and scenting ingredients, pigments, and dyes. Further, the liquid medicine may include arbitrary additives.

According to one aspect, the barrel 3 serving as the main body may have an observation window, or may be formed by a transparent member, so that the internal liquid medicine can be seen. The barrel 3 may also be formed of glass, because glass has sealability and does not have any influence on the liquid medicine.

The communication needle 8 may be made of metal because it may need to penetrate the fixed gasket 2 and to drill a hole in the bag 9.

Example of Use of Liquid-Medicine Discharging Device

FIGS. 9A to 9E are schematic views showing the shape and operation of a liquid medicine cartridge including a discharging head and a liquid medicine reservoir. According to aspects of the present invention, the liquid medicine cartridge is constituted by at least the discharging head, a communicating portion, and the liquid medicine reservoir. For example, the liquid medicine reservoir may have the shape shown in FIG. 3B.

Figure 9A:
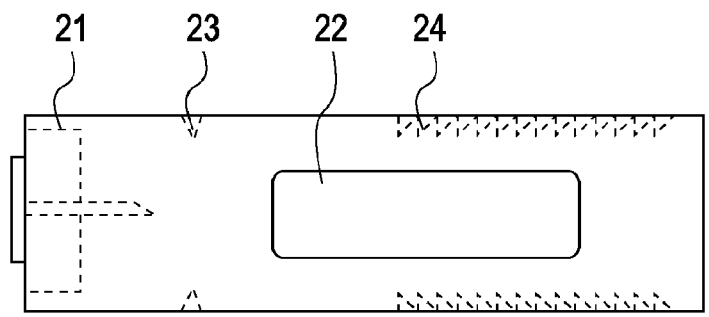

FIG. 9A is a schematic view showing the outer appearance of an embodiment of the liquid medicine cartridge. The discharging head and the communication needle are set in a cartridge casing 21. The cartridge casing 21 may be shaped like a column or a rectangular parallelepiped, or may have a polygonal asymmetric portion that allows the cartridge to be mounted in a predetermined orientation in a liquid-medicine discharging device. The cartridge casing 21 has an observation window 22 through which the user can check the degree of decrease in amount of the liquid medicine. The cartridge casing 21 also includes a holding member 23 and removal preventing notches 24 that also function as a shake preventing guide for a liquid medicine reservoir 1 so that the liquid medicine reservoir 1 translates in the cartridge casing 21 to communicate with the communication needle 8. The holding member 23 and the removal preventing notches 24 can be formed of the same material as that of the cartridge casing 21, for example, resin or metal. The removal preventing notches 24 may be shaped in a manner such that the liquid medicine reservoir 1 moves in a direction toward the inner side of the cartridge casing 21, but does not move in a direction to come out of the cartridge casing 21. For that purpose, the removal preventing notches 24 may be provided on both the inner side of the cartridge casing 21 and the outer side of the liquid medicine reservoir 2. Although the holding member 23 is provided inside the cartridge casing 21 in the figures, it may also be provided in the liquid medicine reservoir 1. At least three holding members 23 may be provided in the cartridge casing 21 so as to hold the liquid medicine reservoir 1. For the same reason, it may be that the removal preventing notches 24 are provided at least three positions.

Figure 9B:
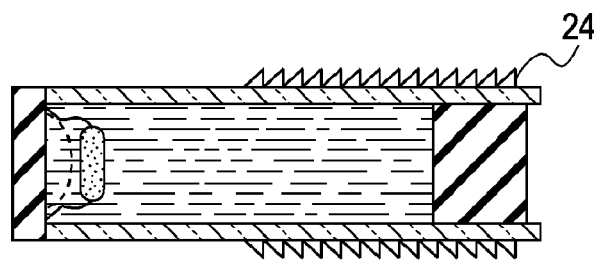

FIG. 9B is a conceptual view of the liquid medicine reservoir 1. As described above, the removal preventing notches 24 may be provided on the outer periphery of the liquid medicine reservoir 1.

Figure 9C:
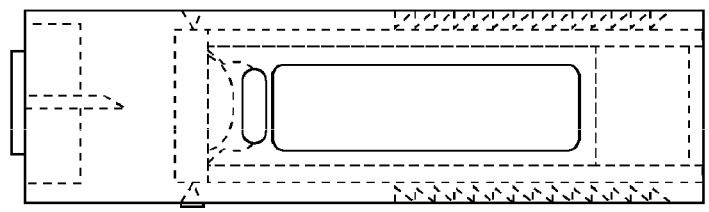

FIG. 9C is a conceptual view showing a state in which the liquid medicine reservoir 1 is set in the cartridge casing 21. In this state, the bag 9 is not seen through the observation window 22.

Figure 9D:
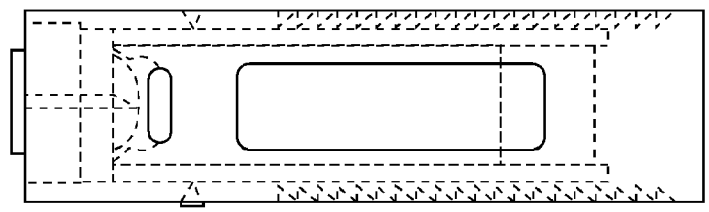

FIG. 9D is a conceptual view showing a state in which the discharging head 6 and the liquid medicine reservoir 1 are connected to each other.

Figure 9E:
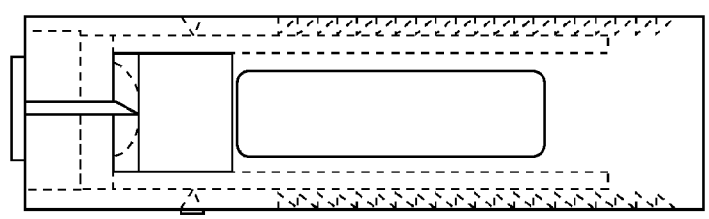

FIG. 9E is a cross-sectional view showing a state in which the movable gasket 4 further moves and the communication needle 8 breaks the bag 9 after the liquid medicine 5 is taken (e.g., inhaled) a specified number of times. The movable gasket 4 is not seen through the observation window 22, and this allows the user to visually recognize that the user has taken (inhaled) the liquid medicine 5 the specified number of times. Further, the bag 9 is pushed by the movable gasket 4, the mesh 9 is deformed, and the bag 9 is broken by the communication needle 8. The discharging inhibitor 10 leaks from the bag 9, and makes discharging impossible.

Figure 10:
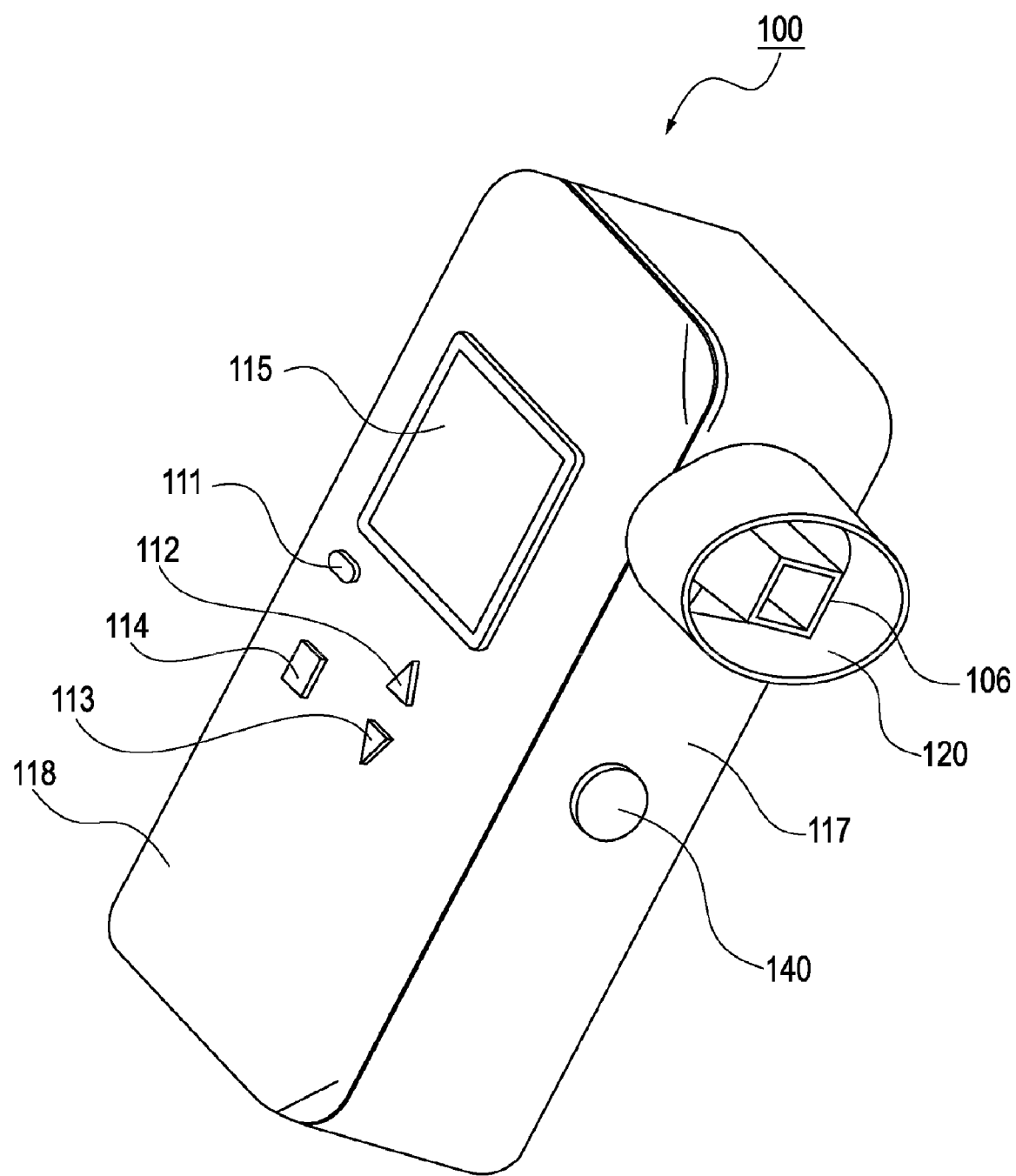
Figure 11:
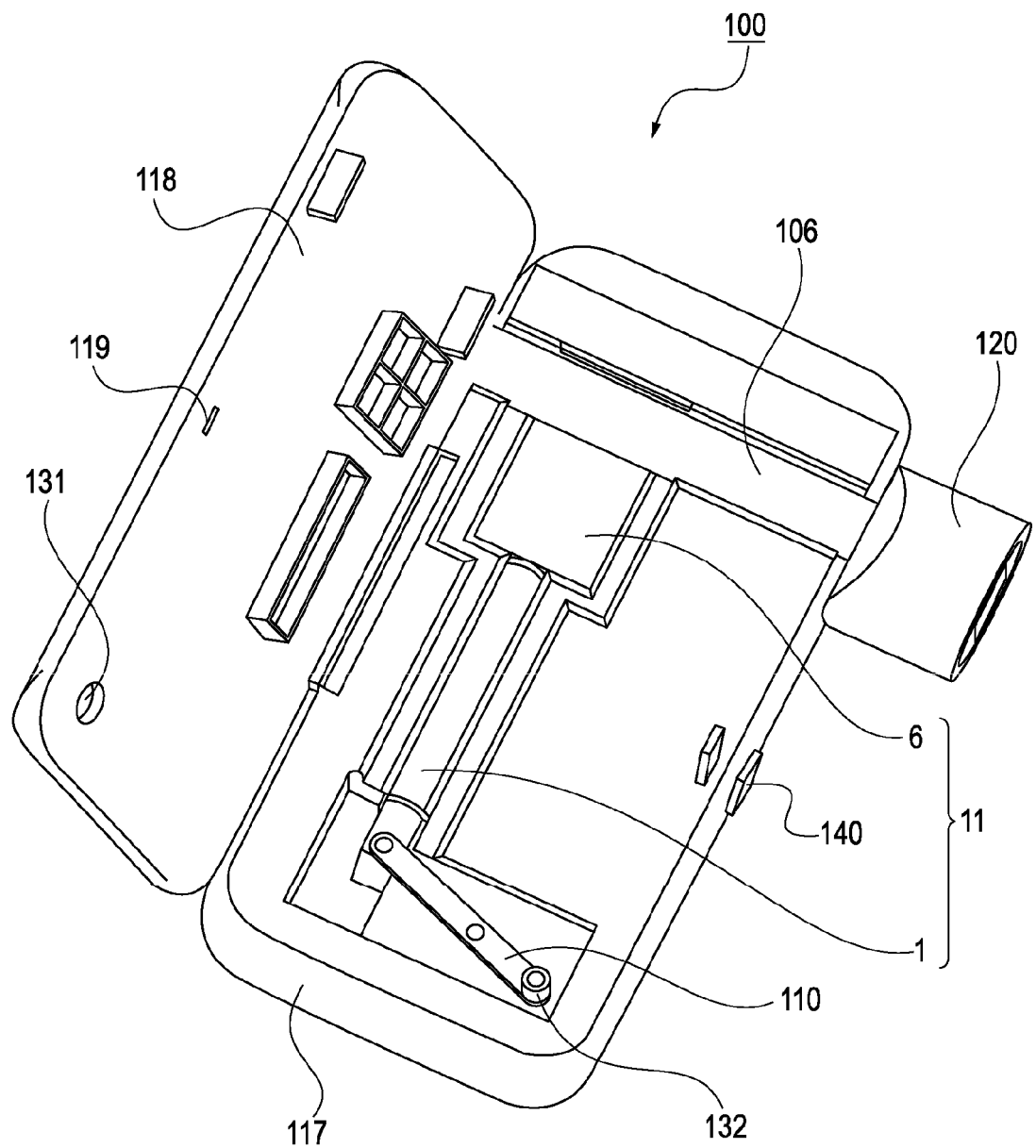

A specific example of a discharging device for liquid medicine to be inhaled that employs the liquid medicine reservoir according to the embodiment will be described with reference to FIGS. 10 and 11. FIG. 10 is a perspective view showing the outer appearance of a liquid-medicine discharging device 100 to which the liquid medicine cartridge 11 of the embodiment is applied. The liquid-medicine discharging device 100 helps the user to inhale the liquid medicine. FIG. 11 is a perspective view showing a state in which an access cover 118 is open in the liquid-medicine discharging device 100.

Referring to FIGS. 10 and 11, the liquid-medicine discharging device 100 has a main outer housing defined by a housing case 117 and the access cover 118. A hook portion 119 of the access cover 118 is engaged with a hook catching portion of the housing case 117 so that the access cover 118 will not open during use, and the hook portion 119 operates together with a lock release button 140 biased by a spring (not shown). To open the access cover 118, the hook portion 119 is disengaged by pressing the lock release button 140, so that the access cover 118 is opened by the force of the spring acting in the opening direction.

The housing case 117 is provided with a suction port (inlet) 120 having an air passage 106, and the lock release button 140 for unlocking the access cover 118. The access cover 118 is provided with a display unit 115 for displaying the dose, time, error, etc., a menu switch button 111 for user setting, an up button 112, a down button 113, and an enter button 114. The suction port 120 is generally called a mouthpiece.

FIG. 11 shows a state in which the access cover 118 of the liquid-medicine discharging device 100 is open. When the access cover 118 is open, a discharging head 6 serving as a liquid-medicine discharging portion removably mounted in the device body and a liquid medicine reservoir 1 serving as a liquid medicine containing portion can be seen. The discharging head 6 discharges the liquid medicine to the air passage 106. The user can inhale the liquid medicine discharged into the air passage 106 by breathing through the suction port 120. In the liquid-medicine discharging device 100 of the embodiment, the suction port 120 and the air passage 106 are provided integrally.

The above-described suction port 120 may be disposed of after each use, or may be cleaned after inhalation to be reused. The liquid medicine cartridge is replaced when the amount of liquid medicine in the liquid medicine reservoir 1 becomes smaller than the amount of medicine to be inhaled at one time. For example, the device body may have a function of counting the discharging amount, and the amount of remaining liquid medicine can be calculated by the discharging-amount count function. Therefore, it is possible to inform the user of the replacement time so as to urge the user to replace the liquid medicine cartridge, or to prohibit discharging until replacement is completed. After the discharging head 6 and the liquid medicine reservoir 1 are mounted, they may be connected by moving the liquid medicine reservoir 1 toward the discharging head 6 by a connecting lever 110, thereby forming a liquid medicine passage through which the liquid medicine flows from the liquid medicine reservoir 1 into the discharging head 6. Since the volume of the liquid medicine 5 is decreased by repeating discharging of the liquid medicine 5, the movable gasket 4 is moved toward the discharging head 6 by the connecting lever 110. This operation can be performed in accordance with the amount and number of times of discharging of the liquid medicine 5.

The liquid-medicine discharging device 100 can be programmed to perform a sequence for preventing reuse of the discharging head 6 and the liquid medicine reservoir 1 by further moving the connecting lever 110 and causing the communication needle 8 to break the bag 9 after the liquid medicine 5 is discharged a specified number of times.

A control unit that controls the power to be supplied to the discharging-energy generating element (heater) of the discharging head may control an applied voltage so that overcurrent passes through the heater when the discharging inhibitor enters the discharging head. The discharging inhibitor can be changed in its nature by heat applied by this operation, and this can reliably clog the nozzle. Entry of the discharging inhibitor into the discharging head can also be detected by an arbitrary method. For example, when the discharging inhibitor is released by forcibly moving the movable gasket 4 by the connecting lever 110 after the liquid medicine is discharged the specified number of times, the movement can be detected. When the discharging inhibitor is released after the liquid medicine runs out, the amount of remaining liquid medicine can be known by comparing the preset amount of liquid medicine with the sum of measured amounts of discharged liquid medicine.

A connecting-lever lock hole 131 is provided in a back surface (see FIG. 11) of the access cover 118. When the access cover 118 is closed, a knob 132 of the connecting lever 110 engages with the connecting-lever lock hole 131, whereby the discharging head 6 and the liquid medicine reservoir 1 are not disconnected unless the access cover 118 is opened. Hence, the discharging head 6 and the liquid medicine reservoir 1 can be prevented from falling off, for example, when carried in baggage.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-244193 filed Sep. 24, 2008, which is hereby incorporated by reference herein in its entirety.

What is claimed is:

1. A liquid medicine reservoir used for an ink-jet inhaler that supplies liquid medicine to a liquid-medicine discharging portion by discharging the liquid-medicine by utilizing a discharging principle of an inkjet method via a communicating portion, the reservoir comprising:
   a cylindrical body configured to hold the liquid medicine therein;
   a first sealing portion to which the communicating portion is connected, the first sealing portion sealing the cylindrical body;
   a second sealing portion configured to seal an end of the cylindrical body opposite the first sealing portion;
   a discharge inhibiting member containing a substance configured to inhibit discharging of the liquid medicine stored in a space in the cylindrical body that is on an inner side of the second sealing portion; and
   an area member connected to the discharge inhibiting member and the first sealing member that is configured to regulate an area occupied by the discharge inhibiting member in the cylindrical body,
   wherein at least one of the first sealing portion and the second sealing portion move relative to each other in accordance with an amount of the liquid medicine.

2. The liquid medicine reservoir according to claim 1, wherein the first sealing portion is fixed to the cylindrical body, and the second sealing portion moves in accordance with the amount of the liquid medicine.

3. The liquid medicine reservoir according to claim 1, wherein the discharge inhibiting member containing the substance configured to inhibit discharging of the liquid medicine is a bag.

4. The liquid medicine reservoir according to claim 3, wherein the bag is fixed in the cylindrical body.

5. The liquid medicine reservoir according to claim 1, wherein the substance configured to inhibit discharging of the liquid medicine is liquid and has a viscosity of 3 mPa·s or more.

6. The liquid medicine reservoir according to claim 1, wherein the substance configured to inhibit discharging of the liquid medicine includes at least one of a water-absorbing polymer, a gelatinizer, and a thickening agent.

7. The liquid medicine reservoir according to claim 1, wherein the liquid medicine is visible from the outside of the cylindrical body, and the substance configured to inhibit discharging of the liquid medicine includes pigment or dye.

8. A discharging device for liquid medicine to be inhaled, the discharging device comprising the liquid medicine reservoir, the liquid medicine discharging portion, and the communicating portion according to claim 1.

* * * * *